(12) United States Patent
Wang et al.

(10) Patent No.: US 10,653,355 B2
(45) Date of Patent: May 19, 2020

(54) NON-INVASIVE VISUALIZATION AND QUANTIFICATION OF NATURAL PIGMENTS

(71) Applicant: THE GENERAL HOSPITAL CORPORATION, Boston, MA (US)

(72) Inventors: Hequn Wang, Boston, MA (US); Conor L. Evans, Boston, MA (US); Sam Osseiran, Boston, MA (US); David E. Fisher, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 271 days.

(21) Appl. No.: 15/545,488

(22) PCT Filed: Feb. 5, 2016

(86) PCT No.: PCT/US2016/016796
§ 371 (c)(1),
(2) Date: Jul. 21, 2017

(87) PCT Pub. No.: WO2016/127065
PCT Pub. Date: Aug. 11, 2016

(65) Prior Publication Data
US 2018/0000406 A1 Jan. 4, 2018

Related U.S. Application Data

(60) Provisional application No. 62/112,401, filed on Feb. 5, 2015.

(51) Int. Cl.
A61B 5/00 (2006.01)
G01J 3/44 (2006.01)
(Continued)

(52) U.S. Cl.
CPC ............ *A61B 5/443* (2013.01); *A61B 5/0075* (2013.01); *A61B 5/444* (2013.01); *G01J 3/44* (2013.01);
(Continued)

(58) Field of Classification Search
CPC combination set(s) only.
See application file for complete search history.

(56) References Cited

U.S. PATENT DOCUMENTS 5,371,368 A * 12/1994 Alfano ................. A61B 5/0091
250/341.1
6,151,522 A 11/2000 Alfano et al.
(Continued)

FOREIGN PATENT DOCUMENTS

WO 2014/011466 A1 1/2014

OTHER PUBLICATIONS

International Search Report for Application No. PCT/US2016/016796 dated Apr. 15, 2016.

*Primary Examiner* — Sean P Dougherty
(74) *Attorney, Agent, or Firm* — Tarolli, Sundheim, Covell & Tummino LLP

(57) ABSTRACT

A system for visualizing melanin present in tissue can include an imaging system to record a signal based on a presence of melanin in tissue and a display device to display an image based on the signal. A first laser source can emit a Stokes pulse train and a second laser source can emit a pump pulse train. Both the first laser source and the second laser source comprise a tunable center wavelength or frequency. An energy difference between a frequency of the Stokes pulse train and a frequency of the pump pulse train is from 1750 cm$^{-1}$ to 2250 cm$^{-1}$. The Stokes and the pump pulse train overlap in space and time. A scanning mechanism focuses the combined Stokes pulse train and pump pulse
(Continued)

train within the tissue and scans across the tissue. A detector detects the signal based on a presence of melanin within the tissue.

20 Claims, 11 Drawing Sheets

(51) Int. Cl.
    *G01N 21/88*     (2006.01)
    *G01N 21/17*     (2006.01)
    *G01N 21/41*     (2006.01)
    *G01N 21/65*     (2006.01)

(52) U.S. Cl.
    CPC . *G01N 21/8851* (2013.01); *G01N 2021/1765* (2013.01); *G01N 2021/418* (2013.01); *G01N 2021/655* (2013.01)

(56) References Cited

U.S. PATENT DOCUMENTS

| | | | |
|---|---|---|---|
| 7,039,452 B2 | 5/2006 | McClane et al. | |
| 7,586,618 B2* | 9/2009 | Marks | G01J 3/4412 356/451 |
| 7,623,908 B2* | 11/2009 | Boppart | G01J 3/44 600/477 |
| 7,751,057 B2* | 7/2010 | Oldenburg | A61B 5/0066 356/497 |
| 7,787,129 B2* | 8/2010 | Zysk | A61B 5/0084 356/481 |
| 8,432,543 B2 | 4/2013 | Frankel | |
| 8,792,156 B1* | 7/2014 | Kieu | G01J 3/44 356/301 |
| 9,634,454 B1* | 4/2017 | Kieu | H01S 3/0092 |
| 2007/0152154 A1* | 7/2007 | DeCamp | G01J 3/2803 250/339.07 |
| 2008/0037595 A1 | 2/2008 | Gankkhanov et al. | |
| 2010/0188496 A1 | 7/2010 | Xie et al. | |
| 2013/0043392 A1* | 2/2013 | Mildren | H01S 3/30 250/341.1 |
| 2013/0149734 A1 | 6/2013 | Ammar et al. | |
| 2013/0162994 A1* | 6/2013 | Xie | G01N 21/171 356/342 |
| 2014/0197335 A1* | 7/2014 | Jayasooriya | G01N 21/65 250/459.1 |
| 2014/0200434 A1 | 7/2014 | Cheng | |
| 2014/0328365 A1* | 11/2014 | Grujic | H01S 3/091 372/70 |
| 2014/0350534 A1 | 11/2014 | Kircher et al. | |
| 2016/0103307 A1* | 4/2016 | Frankel | G02B 21/0076 600/317 |

* cited by examiner

NON-INVASIVE VISUALIZATION AND QUANTIFICATION OF NATURAL PIGMENTS

RELATED APPLICATIONS

This application claims the benefit of U.S. Provisional Application No. 62/112,401, filed Feb. 5, 2015, entitled "Non-Invasive Visualization and Quantification of Natural Pigments," the entirety of which is hereby incorporated by reference for all purposes.

TECHNICAL FIELD

The present disclosure relates generally to non-invasive visualization and quantification of natural pigments and more specifically to systems and methods for imaging tissue to non-invasively visualize and quantify natural pigments therein.

BACKGROUND

Fair-skinned individuals are at a higher than average risk of developing melanoma, a cancer that develops from melanin-producing cells known as melanocytes. Melanin is a general term, encompassing eumelanin (brown/black pigments) and pheomelanin (red/blond pigments) and various mixtures of these species. Recent evidence suggests that the red/blond pheomelanin pigment may have UV-radiation-independent as well as UV-exacerbated pro-oncogenic roles, leading to the formation of pre-malignant lesions that are challenging to diagnose by physician exam due to their lack of visible color. Therefore, the ability to identify and characterize pheomelanin within skin has emerged as a critical need, both to improve understanding of the underlying biology of these pre-malignant lesions and to refine diagnostic strategies for melanoma. In addition, certain melanoma lesions are characterized by variability of coloration, with regions that are light or unpigmented—thereby potentially representing similar pheomelanin-containing but poorly visualized regions of melanoma growth.

SUMMARY

The present disclosure relates generally to non-invasive visualization and quantification of natural pigments. More specifically, the present disclosure relates to systems and methods for imaging tissue to non-invasively visualize and quantify natural pigments therein. In some examples, a vibrational imaging technique, such as coherent anti-Stokes Raman scattering (CARS) imaging, can selectively tune into molecular vibrations of the pigments to visualize the pigments selectively without requiring labels. For example, vibrational imaging can be used to non-destructively and non-invasively visualize, characterize, and distinguish between different melanin pigments (e.g., red/blond pheomelanin pigments and brown/black eumelanin pigments) in cells and tissues.

An aspect of the present disclosure relates to a system comprising an imaging system to record a signal based on a presence of melanin in tissue and a display device to display an image based on the signal. The imaging system includes a laser source to emit a Stokes beam comprising a tunable center wavelength or frequency. The imaging system also includes a laser source to emit a pump beam comprising a tunable center wavelength or frequency. The Stokes beam and the pump beam can be configured such that an energy difference between a frequency of the Stokes beam and a frequency of the pump beam is from 1750 cm$^{-1}$ to 2250 cm$^{-1}$. The Stokes beam and the pump beam overlap in space and time to image the tissue. The imaging system also includes a scanning mechanism to focus the combined Stokes beam and pump beam within the tissue and scan across the tissue and a detector to detect the signal based on a presence of melanin within the tissue. The image can be constructed based on the detected signal and displayed by the display device.

Another aspect of the present disclosure relates to a method for displaying an image based on a recorded signal. The method includes configuring a laser source to deliver a Stokes beam and another laser source to deliver a pump beam. An energy difference between frequency of the Stokes beam and a frequency of the pump beam is between 1750 cm$^{-1}$ to 2250 cm$^{-1}$. The method also includes irradiating tissue with the Stokes beam and the pump beam focused within the tissue. The Stokes beam and the pump beam overlap in space and time. The method also includes detecting a signal based on a presence of melanin within the tissue; and displaying an image based on the signal to visualize the melanin within the tissue.

A further aspect of the present disclosure relates to a portable imaging probe. The portable imaging probe includes a scanning mechanism to focus a Stokes beam and a pump beam within tissue while scanning across the tissue. An energy difference between a frequency of the Stokes beam and a frequency of the pump beam is from 1750 cm$^{-1}$ to 2250 cm$^{-1}$. The Stokes beam and the pump beam overlap in space and time to image the tissue. The portable imaging probe also includes a detector to detect a signal based on a presence of melanin within the tissue.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 6 (*a*) shows a trans-illumination image acquired with the 877 nm pump beam, (b) shows a confocal fluorescence image of tdTomato, (c) shows a false color CARS image acquired with pump ($\lambda_P$=877 nm) and Stokes beams ($\lambda_S$=1064 nm), (d) shows a false color image acquired using the pump beam only, showing prominent two-photon fluorescence signals, (e) shows a false color image acquired using the Stokes beam only, showing weak two-photon fluorescence signals, and (f) shows a false color image illustrating the true CARS signal obtained by subtracting fluorescence of (d) and (e) from (c)

DETAILED DESCRIPTION

I. Definitions

Figure 1:
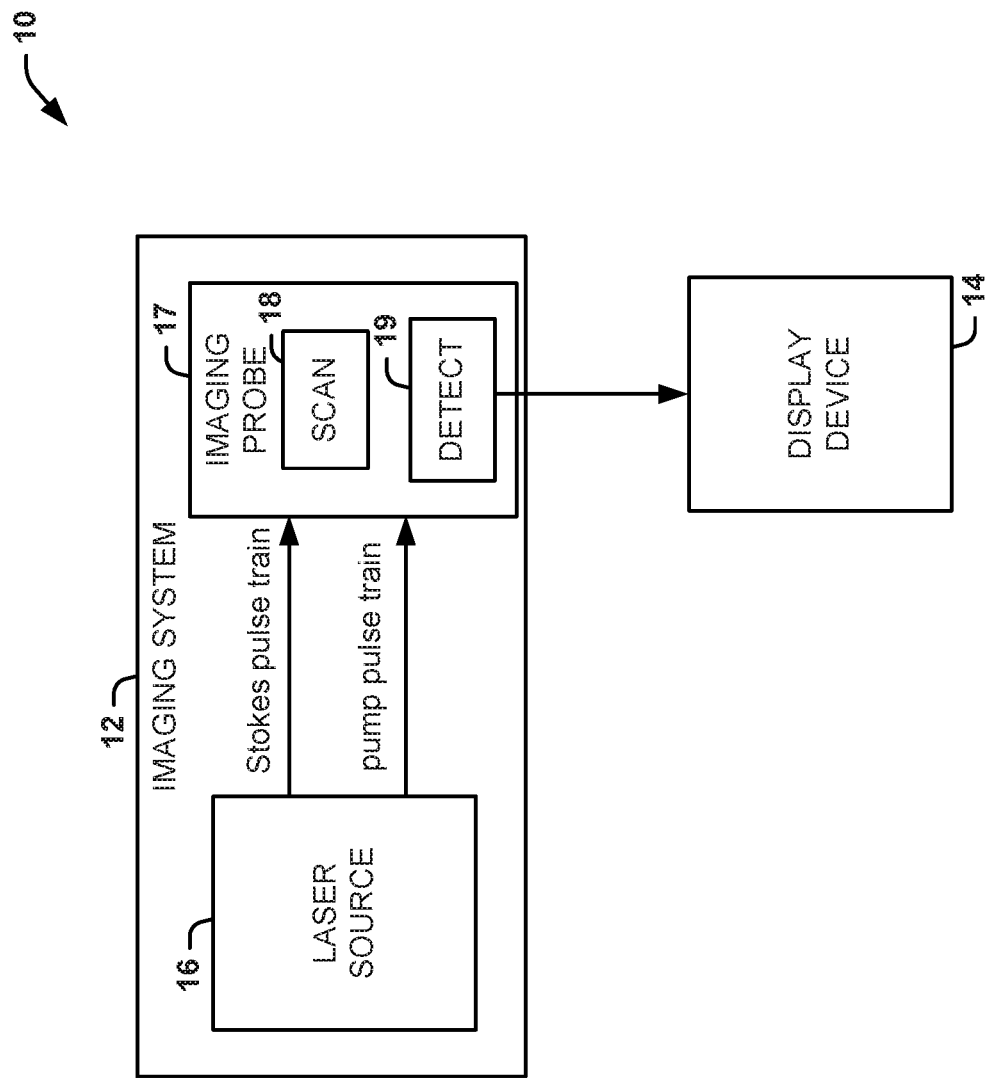
FIG. 1 is a block diagram showing an example of a system that can image tissue to non-invasively visualize and quantify natural pigments therein in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "vibrational imaging" can refer to a technique that generates images based on vibrational signatures of molecules. Notably, vibrational imaging does not require labeling to acquire molecular specific information.

As used herein, the term "coherent Raman scattering" can refer to a vibration imaging technique in which two coherent electromagnetic fields (e.g., beams of laser light) exhibit a frequency difference matching the vibration frequency signature of a molecule. Coherent Raman scattering can include coherent anti-Stokes Raman scattering (CARS) and simulated Raman scattering (SRS).

As used herein, the term CARS can refer to a vibrational imaging technique in which two coherent beams of laser light, referred to as the "pump" beam and the "Stokes" beam, are shined into a sample. When the pump beam and the Stokes beam exhibit a frequency difference that matches the vibration frequency signature of a specific molecule in the sample, a CARS signal (e.g., including newly generated photons) can be generated at a new detectable frequency, which can be used to generate a chemically weighted image.

As used herein, the term SRS can refer to a complimentary process to the CARS process, which causes an intensity increase in the Stokes beam and an intensity decrease in the pump beam. A SRS signal can be generated based on the intensity changes in the Stokes beam and the pump beam.

As used herein, the term "modulation transfer signal" can refer to a signal where an intensity or phase modulation of the Stokes or pump beam can, through an interaction with the sample, transfer that modulation to the other beam. For example, an intensity modulation of the Stokes beam could be transferred to the pump beam at regions in the sample containing an absorbing molecule.

As used herein, the term "signal" can refer to one or more output signals that can be used to generate an image. For example, the signal can include one or more of a CARS signal, a SRS signal, or a modulation transfer signal.

As used herein, the term "laser source" can refer to a system of one or more devices that produces a nearly parallel, nearly monochromatic, and coherent beam of light.

As used herein, the term "beam" of light from a laser source can refer a series or train of pulses from a pulsed laser source. The terms "beam" and "pulse train" can be used interchangeably herein.

As used herein, the term "natural pigment" can refer to one or more molecules that give coloring to an animal or a plant.

As used herein, the term "melanin" can refer to a group of natural pigments produced by cells. For example, melanin can include eumelanin (brown/black pigments) and pheomelanin (red/blond pigments).

As used herein, the term "melanoma" can refer to a type of cancer that develops from pigment-producing cells known as melanocytes.

As used herein, the term "non-destructive" imaging can refer to an imaging modality that does not cause changes to tissue being imaged.

As used herein, the term "non-invasive" imaging can refer to an imaging modality that does not require the introduction of instruments into the body, other than through natural orifices.

As used herein, the terms "nevus" or "nevi" can refer to one or more benign chronic lesions (e.g., moles) in the skin or mucosa, where the cellular content is predominantly composed of melanocytes.

As used herein, the term "sample" can refer to cells or tissues from or in a patient to be imaged. The cells or tissues can be imaged in vivo, in vitro or in situ. The terms "sample" and "tissue" may be used interchangeably herein.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to non-invasive visualization and quantification of natural pigments. More specifically, the present disclosure relates to systems and methods for imaging tissue to non-invasively visualize and quantify natural pigments therein. Using a vibrational imaging technique, like coherent anti-Stokes Raman scattering (CARS), which can selectively tune into molecular vibrations of the pigments, the pigments can be selectively visualized without the need for labeling the pigments. Advantageously, CARS imaging offers a specific, direct, and facile route for the visualization, detection, and characterization of different melanin pigments (red/blond pheomelanin pigments and brown/black eumelanin pigments) in vivo non-destructively and non-invasively in real-time.

The label-free nature of CARS microscopy is based on the ability to selectively tune into a specific molecular vibrational mode. CARS imaging can tune into a specific molecular vibrational mode using two coincident laser beams, where the shorter wavelength sources are termed the pump beams and the longer wavelength sources are termed the Stokes beams. The wavelength mismatch between the two sources thus creates an oscillating beat frequency that, when tuned to match a particular Raman vibrational mode, induces a coherent macroscopic polarization at the objective focus. An additional pump photon may interact with this macroscopic polarization to produce anti-Stokes photons that are intrinsically blue-shifted relative to the incident beams. Thus, the coherently scattered anti-Stokes light is collected to create label-free images of particular chemical species. For example, by exploiting a previously identified Raman vibrational band at 2000 $cm^{-1}$ that is unique to pheomelanin, CARS imaging can be used to detect pheomelanotic/invisible melanomas, premalignant cutaneous lesions, or regions of inhomogeneity in darkly pigmented lesions that would more accurately define the margins of malignant melanoma lesions. Moreover, CARS imaging can be used to study and understand the UV-independent melanoma pathway and to refine diagnostic strategies for potentially pre-malignant "invisible" nevi. In some instances, SRS or modulation transfer imaging can be performed in concert with the CARS imaging to provide images that distinguish between pheomelanin and eumelanin to provide a greater diagnostic and prognostic ability.

III. Systems

As shown in FIG. 1, one aspect of the present disclosure can include a system 10 that can image tissue to non-invasively visualize and quantify natural pigments within the tissue. One example of a natural pigment that resides in the tissue is melanin (including red/blond pheomelanin pigments and brown/black eumelanin pigments). The imaging provided by the system 10 is non-destructive to melanin within the tissue. Accordingly, the system 10 can be used for applications, including detection of melanoma, defining the margins of malignant melanoma lesions, refining diagnostic strategies for potentially pre-malignant "invisible" nevi, providing greater prognostic ability, and the like.

The system 10 can include an imaging system 12 and a display device 14. The imaging system 10 can provide vibrational imaging of the natural pigment. In some instances, the vibrational imaging can include CARS, in which two coherent beams (e.g., Stokes beam and pump beam) of light are tuned to exhibit a frequency difference that matches the vibration frequency signature of the natural pigment so that a CARS signal including newly generated photons can be generated at a new detectable frequency. In other instances, the vibrational imaging can use SRS in combination with CARS. SRS is complimentary to CARS and based on an increase in intensity of the Stokes beam and the decrease in intensity of the pump beam. In still other instances, the two beams can provide modulation transfer imaging.

The imaging system 10 can include a laser source 16 and an imaging probe 17. The laser source 16 can include a first laser light source to supply the Stokes beam and a second laser light source to supply the pump beam. In some instances, the first laser light source and the second laser light source can be included in separate devices. In other instances, the first laser light source and the second laser light source can be included within the same device. The first laser source and the second laser source can be configured such that a frequency of the Stokes beam and a frequency of the pump beam have an energy difference specific to the natural pigment being imaged.

The laser source 16 can be used to selectively tune the Stokes beam and/or the pump beam can be selectively tuned into molecular vibrations of the natural pigment of interest. For example, when the natural pigment is melanin, the Stokes beam and the pump beam can be tuned for imaging at the 2000 $cm^{-1}$ band. In some instances, the frequency of the Stokes beam and the frequency of the pump beam can have an energy difference from 1750 $cm^{-1}$ to 2250 $cm^{-1}$. In other instances, the frequency of the Stokes beam and the frequency of the pump beam can have an energy difference from 1850 $cm^{-1}$ to 2150 $cm^{-1}$. In still other instances, the frequency of the Stokes beam and the frequency of the pump beam can have an energy difference from 1950 $cm^{-1}$ to 2050 $cm^{-1}$.

The laser source 16 can supply the Stokes beam and the pump beam to the imaging probe 17. The transmission of the beams can be via one or more optical components, including lenses, filters, mirrors, and the like configured in a manner to facilitate the transmission. In some instances, the imaging probe 17 can receive the Stokes beam and the pump beam from the laser source 16 through a fiber optic coupling. In these instances, the imaging probe 17 can be a portable imaging probe that, in some instances, can be handheld. In other instances, the imaging probe 17 can be a microscope.

The imaging probe 17 can be used to scan the tissue to detect a signal corresponding to the natural pigment. Accordingly, the imaging probe 17 can include a scanning mechanism 18 and a detector 19. The scanning mechanism 18 can focus the Stokes beam and pump beam within the tissue and scan across the tissue. The Stokes beam and the pump beam can be combined so that the Stokes beam and the pump beam overlap in space (x, y, z) and time to image the tissue. The beams can be combined at any point in the imaging system 10: in the laser source 16, in the connection between the laser source 16 and the imaging probe 17, or in the imaging probe 17. The combined Stokes beam and pump beam can be configured to cause the natural pigment within the tissue to produce a signal. The detector 19 can detect the signal based on a presence of the natural pigment within the tissue.

The detector 19 can measure the signal in the epi (backwards) direction. As one example, the detector 19 can include a dichroic mirror/filter combination. The dichroic mirror is used to separate the backwards propagating signal from the incident Stokes beam and pump beam. For example, the dichroic mirror can be a 750 nm short-pass mirror. The signal is passed through the filter to eliminate other (unwanted) tissue emissions from being detected. For example, the filter can be a 730 nm, 40 nm bandpass filter. A photomultiplier tube can be used to collect the signal with a high signal-to-noise ratio. As an example, the photomultiplier tube can be a thermoelectrically cooled photomultiplier tube. In another example, the photomultiplier tube can be a wide-area side-on photomultiplier tube. The detector 19 can provide the signal to the display device 14, which can to display an image based on the signal. The image provides a visualization of the natural pigment present in the tissue.

In some instances, the scanning mechanism 18 can provide CARS imaging to the tissue to detect pheomelanin present within the tissue. With CARS imaging, a CARS signal can be generated, corresponding to the newly generated photons upon the combined Stokes and pump beam matching the resonance frequency of pheomelanin. The display device 14 can display an image that includes an indication of the pheomelanin present in the tissue.

In other instances, the scanning mechanism 18 can provide SRS imaging and/or modulation transfer imaging in combination with CARS imaging to improve the sensitivity and selectivity of CARS imaging alone. When performing SRS imaging and/or modulation transfer imaging in combination with CARS imaging of melanin in the tissue, both eumelanin and pheomelanin can be detected and identified in the tissue. While not wishing to be bound by theory, it is believed that this is because the modulation transfer signal does not originate from a vibrational process, like the CARS signal, but rather arises due to the simultaneous absorption of the pump pulse train and the Stokes pulse train by the melanin present in the tissue.

As an example, the detector 19 can include a separate configuration to detect the signal that indicates the SRS or modulation transfer signal. In this situation, the detector 19 can use a lock-in amplifier. When the Stokes beam is modulated, the pump beam is modulated at the same frequency and phase by the interaction of the beams in the sample. For modulation transfer imaging, this is thought to be due to the simultaneous absorption of the pump and Stokes beams, wherein the absorption of either beam is most efficient when the other is present at the same time. This is uniquely different than transient absorption processes as absorption of the two colors is seemingly simultaneous. When the pump beam modulation is detected in the forward direction (away from the objective lens), this novel signal shows contrast when eumelanin or pheomelanin is present. This combination of CARS and the modulation signal can be used to distinguish eumelanin and pheomelanin.

IV. Methods

Figure 2:
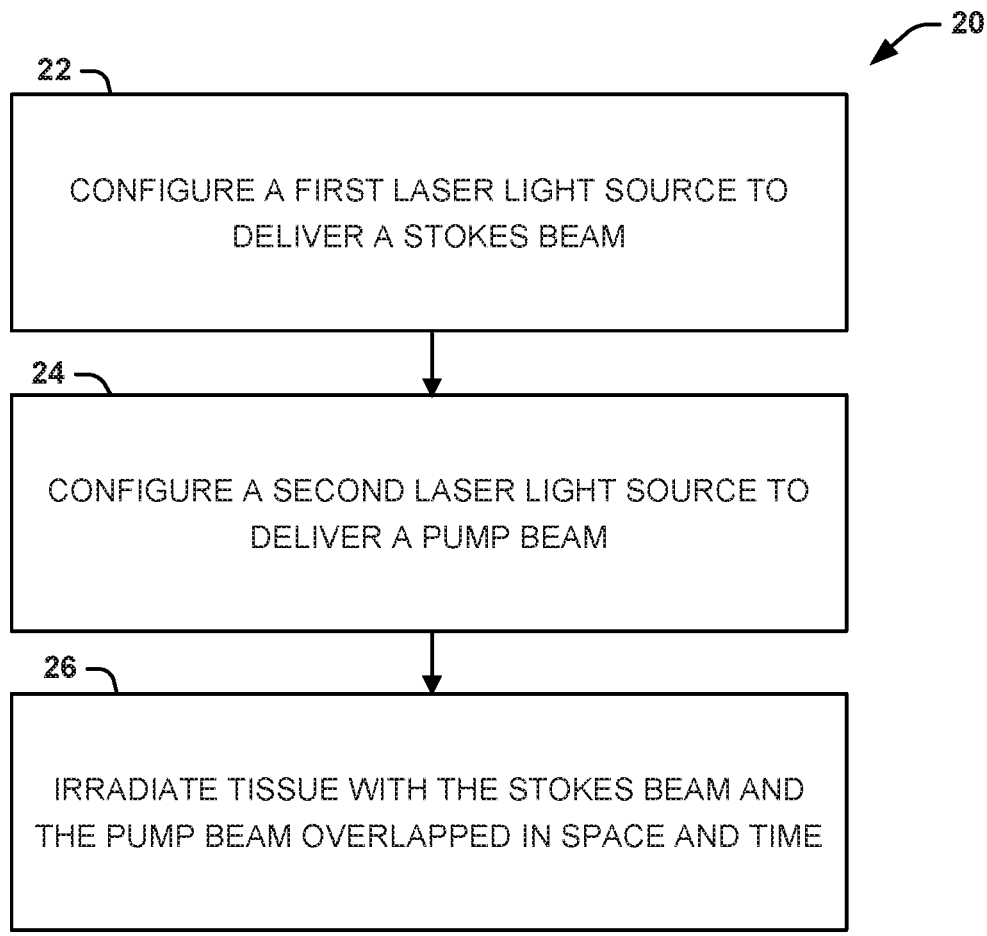
FIGS. 2 and 3 are process flow diagrams showing an example method for imaging tissue to non-invasively visualize and quantify natural pigments therein according to an aspect of the present disclosure.
Figure 3:
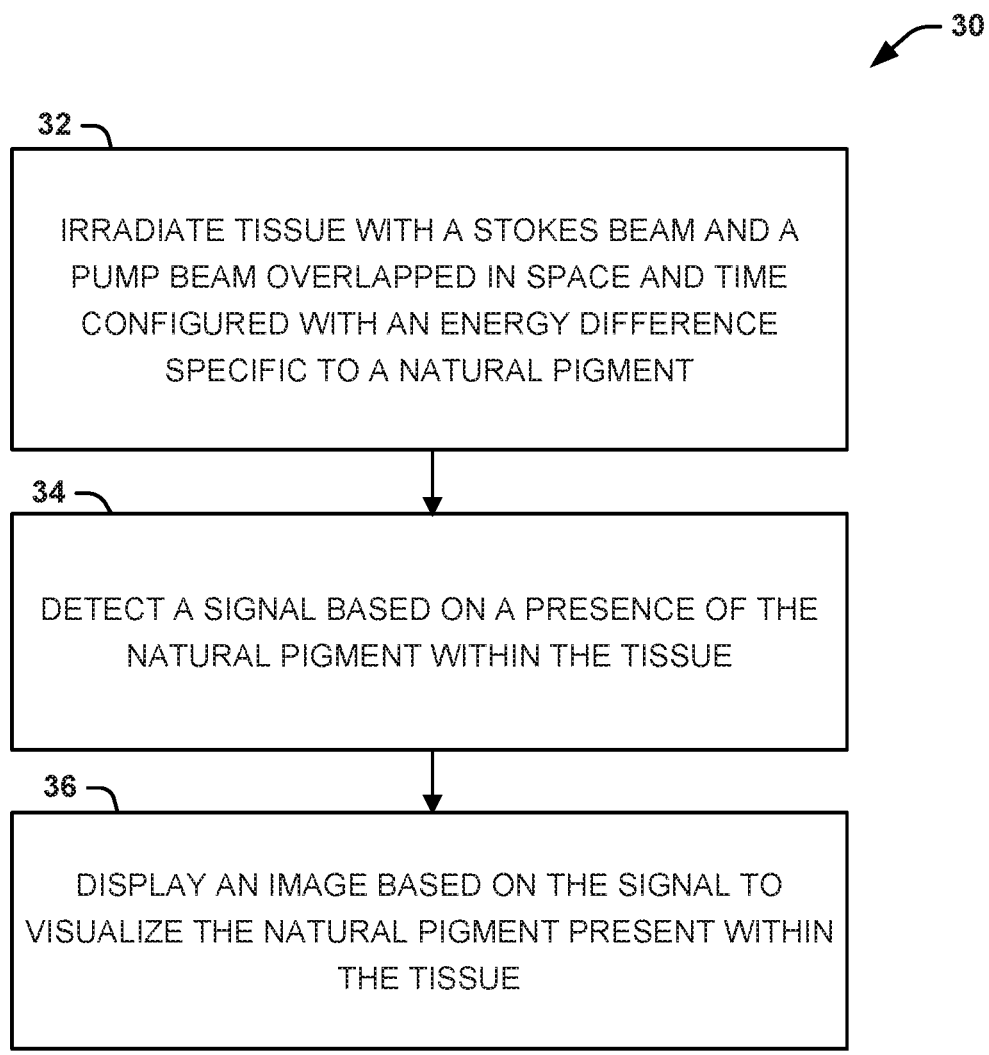

Another aspect of the present disclosure can include methods for imaging tissue to non-invasively visualize and quantify natural pigments therein. One example of a natural pigment that can be imaged in this manner is melanin (red/blond pheomelanin pigments and/or brown/black eumelanin pigments). A method 20 for configuring an imaging procedure to non-invasively visualize and quantify natural pigments in tissue is shown in FIG. 2. A method 30 for conducting the imaging procedure to non-invasively visualize and quantify natural pigments in tissue is shown in FIG. 3. The methods 20, 30 can be executed, for example, by the system 10 shown in FIG. 1.

The methods 20 and 30 of FIGS. 2 and 3, respectively, are illustrated as process flow diagrams with flowchart illustrations. For purposes of simplicity, the methods 20 and 30 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 20 and 30.

Referring to FIG. 2, illustrated is a method 20 for configuring an imaging procedure to non-invasively visualize and quantify natural pigments in tissue. At 22, a first laser light source can be configured to deliver a Stokes beam. At 24. A second laser light source can be configured to deliver a pump beam. In one example, the first laser light source and the second laser light source can be separate devices. In another example, the first laser light source and the second laser light source can be within the same device. The first laser source and the second laser source can be configured to such that a frequency of the Stokes beam and a frequency of the pump beam have an energy difference specific to the natural pigment being imaged.

The Stokes beam and the pump beam can be selectively tuned into molecular vibrations of the natural pigment of interest. For example, when the natural pigment is melanin, the Stokes beam and the pump beam can be tuned for imaging at the 2000 $cm^{-1}$ band. In some instances, the frequency of the Stokes beam and the frequency of the pump beam can have an energy difference from 1750 $cm^{-1}$ to 2250 $cm^{-1}$. In other instances, the frequency of the Stokes beam and the frequency of the pump beam can have an energy difference from 1850 $cm^{-1}$ to 2150 $cm^{-1}$. In still other instances, the frequency of the Stokes beam and the frequency of the pump beam can have an energy difference from 1950 $cm^{-1}$ to 2050 $cm^{-1}$.

Additionally, the Stokes beam can be tuned to a center wavelength selected from 1040 nm to 1064 nm, while the pulp beam can be tuned to a center wavelength selected from 841 nm to 888 nm. In some examples, the Stokes beam can be tuned to a center wavelength selected to be 1040 nm and the pump beam can be tuned to a center wavelength selected to be 855 nm. In some examples, the Stokes beam can be tuned to a center wavelength selected to be 1064 nm and the pulp beam can be tuned to a center wavelength selected to be 871 nm.

Additional parameters that can be configured are as follows:

| | |
|---|---|
| Pulse Duration | |
| Optimal | 90 fs to 7 ps |
| Highly optimal | <150 fs |
| Repetition Rate | |
| 80 MHz | |
| 76 MHz | |
| Chirp | |
| | Unchirpped pulses provided by negative group velocity dispersion optics or positive group velocity dispersion optics. |

At 26, the tissue can be irradiated with the Stokes beam and the pump beam to provide images of the natural pigment in the tissue. The Stokes beam and the pump beam can be configured to overlap in space (x, y, z) and time. The overlap in space and time must be precise in order for a detectable signal to be generated. In some instances, a scanning device can be configured according to the following parameters to image the natural pigment in the tissue, as follows:

| | |
|---|---|
| Power combination at focus for each wavelength | |
| Ratio of power, Pump:Stokes: | ~1.5:1 for non-destructive imaging |
| Actual powers at focus: | Pump 15 mW, Stokes 8 mW |
| Field of View | |
| Optimal | 250 × 250 μm |
| Scanning Speed/Pixel Dwell Time | |
| Non-destructive imaging 2 μs/pixel scan rate | |
| Multiple frames averaged to improve signal to noise | |
| Objective Lenses/NA | |
| Magnification: | 20-60× |

-continued

| | |
|---|---|
| Numerical Aperture | 0.7+ |
| Optimal magnification/NA | 60×/1.2 NA |
| Laser power modulation with depth of imaging | |
| Each 10 μm of depth within the skin requires ~2 mW of additional pump power and ~1.3 mW of additional Stokes power to maintain signal to noise. | |

Referring to FIG. 3, illustrated is a method 30 for conducting the imaging procedure to non-invasively visualize and quantify natural pigments in tissue. At 32, tissue can be irradiated with a Stokes beam and a pump beam (configured as per conditions specified with respect to FIG. 2) overlapped in space and time. At 34, a signal can be detected based on a presence of the natural pigment within the tissue. The signal can arise due to a simultaneous interaction of the Stokes beam and the pump beam with the natural pigment within the tissue. For example, the signal can include a CARS signal, a SRS signal, and/or a modulation transfer signal. In some instances, the signal can include the CARS signal. For example, the CARS signal can distinguish the presence of the natural pigment, pheomelanin. In other instances, the signal can include the CARS signal and the modulation transfer signal or the SRS signal. The CARS signal in combination with the modulation transfer signal or the SRS signal can be used to distinguish between different natural pigments, eumelanin and pheomelanin. The modulation transfer signal or the SRS signal improves sensitivity and selectivity, providing a technical improvement over the CARS signal alone.

At 36, an image can be displayed based on the signal. The image can allow for the visualization of the natural pigment (e.g., melanin) present within the tissue. For example, when the signal includes the CARS signal, the image can include a visualization of pheomelanin within the tissue. In other examples, when the signal includes the CARS signal and the modulation transfer signal or the SRS signal, the image can provide a visualization that distinguishes between pheomelanin and eumelanin within the tissue.

V. Example

The following example is for the purpose of illustration only and is not intended to limit the scope of the appended claims. This example shows that the distribution of pheomelanin in cells and tissues can be visualized and characterized non-destructively and non-invasively with coherent anti-Stokes Raman scattering (CARS) microscopy. Interestingly, the strength of the observed anti-Stokes signal was far greater than anticipated based on the Raman data, which indicates the possibility that the observed signal is resonantly enhanced.

Methods

Mice

Mc1r mutant red-head mice were used due to their elevated risk for the UV-independent, development of melanoma. These Mc1r mice were genetically controlled and engineered to express either tdTomato or GFP on a melanocyte-specific promoter so as to enable FACS isolation of melanocytes.

A conditional, melanocyte-targeted allele of the most common melanoma oncoprotein, $BRAF^{v600E}$ was introduced into mice carrying an inactivating mutation in the Mc1r gene (these mice have a phenotype analogous to red-haired/fair-skin humans). An albino allele was also introduced, which ablates all pigment production on the Mc1r$^{e/e}$ background via a mutation in tyrosinase, a key enzyme in the early stages of melanin synthesis.

CARS Microscopy System

The CARS microscope was built over a customized confocal microscope (Olympus FV1000, Center Valley, Pa.), which has an additional laser entry port to accept external light sources. CARS microscopy was performed in most experiments using a dual output femtosecond pulsed laser system (Spectra-Physics Insight DeepSee, Santa Clara, Calif.), where the first output is tunable from 680 to 1300 nm while the second is fixed at 1040 nm. In other experiments, images were acquired using a pair of infrared picosecond laser sources, where the first is a mode-locked Nd:Vanadate laser (PicoTRAIN, High-Q Laser, Rankweil, Austria) generating 1064 nm pulses with 7 ps duration, while the other is an optical parametric oscillator (Levante, APE, Berlin, Germany) producing tunable 3 ps duration infrared pulses. Thus, to achieve CARS imaging at the reported 2000 cm$^{-1}$ band of pheomelanin with the femtosecond system, the 1040 nm output was chosen as the Stokes beam ($\omega_S$), while the pump beam ($\omega_P$) was set to either 861 nm or 855 nm ($\omega_P-\omega_S=2000$ cm$^{-1}$ or $\omega_P-\omega_S=2081$ cm$^{-1}$), thus generating anti-Stokes signals at 735 nm or 726 nm, respectively. In the case of the picosecond system, the 1064 nm output was chosen as the Stokes beam ($\omega_S$), while the pump beam was set to 877 nm ($\omega_P-\omega_S=2000$ cm$^{-1}$), thus generating an anti-Stokes signal at 746 nm. A half-wave plate and a polarizer were placed at the each of the two laser outputs to adjust beam power. To focus the beams onto the sample, a 1.20 NA 60× water immersion microscope objective (Olympus UPLSAPO 60XW, Center Valley, Pa.) was used. CARS signal detection was achieved using both a shortpass and a bandpass filter (Chroma ET750sp-2p8 and ET730/40m, Bellows Falls, Vt.) placed in front of a thermoelectrically cooled photomultiplier tube (Hamamatsu H7422PA-50, Hamamatsu City, Japan). The sum power of the two beams at the objective was less than 10 mW for all experiments performed in this study.

Preparation of Synthetic Pheomelanin

Pheomelanin was synthesized following the protocol published by d'Ischia et al., Melanins and melanogenesis: methods, standards, protocols. Pig cell & melanoma res, 26(5):616-33, 2013. The synthesized pheomelanin was then lyophilized to yield a dense, reddish-brown powder. To emulsify the pheomelanin, a small quantity (~0.1 mg) was placed in a 2 mL microcentrifuge tube, to which 1 mL H$_2$O and 0.25 mL hexane were added. The resulting mixture was sonicated for two cycles of three minutes each to generate an emulsion of pheomelanin microparticles. The sample was then sandwiched between a glass slide and a coverslip with an imaging spacer (Grace Bio-Labs Secure-Seal, Bend, Oreg.). To prevent sample evaporation, the edges of the coverslip were sealed to the glass slide with nail polish.

CARS Spectral Data Acquisition and Processing

In order to generate CARS spectra of pheomelanin samples, the pump wavelength was tuned from 841 nm to 871 nm in single nanometer increments. For each wavelength value, 3 images were acquired: the first with only the pump beam, the second with only the Stokes beam, and the third with both. While the first two image sets showed only minimal intensity, they nevertheless correspond to the weak multiphoton fluorescence of pheomelanin and were thus subtracted from the CARS images to isolate the coherent Raman signal. In order to then normalize the CARS signal against a neutral reference, the sample's glass coverslip was also imaged under the same conditions. Glass produces a non-resonant background signal that is invariant across the spectral range of interest, justifying its use as a reference to compensate for wavelength-dependent intensity variations that may arise from the optical components throughout the imaging system.

In order to generate the spectra, the 31 corrected CARS images were first summed together, and the resulting image was binarized to generate a mask. The mask was then applied to all CARS and glass images in order to isolate the regions corresponding to pheomelanin. The masked CARS images were then divided by the masked glass images on a pixel-by-pixel basis, and the resulting ratiometric values were averaged to obtain a single data point for a given wavelength. This process was iterated across all 31 sampled wavelengths, and the resulting spectra were normalized by the area under the curve and multiplied by a factor of 30 (corresponding to n-1 data points) such that a flat spectral response is centered at a normalized value of 1 across the entire spectral range. The experiment was performed in triplicates, where the plotted spectra show the experimental means with the error bars corresponding to one standard deviation. As an added control, the analysis was repeated for the image background by inverting the binary mask generated earlier. Given that the image background signal arises from the non-resonant background generated by the water and hexane emulsion, the analysis performed on the background revealed a flat spectrum centered at 1, as expected.

Melanocyte Extraction

Mice were first sacrificed in order to harvest the skin from their backs. The fat was then trimmed down, and the resulting skin was flattened out on a petri dish. Next, the skin was treated with 2 mL of Dispase solution to enable peeling off the epidermis, which was subsequently trypsinized to break apart the cells. The trypsin was then neutralized with cell media, and the resulting cell solution was stained with a FITC-tagged antibody targeting c-Kit, a specific surface marker for melanocytes. The cells were then sorted with FACS based on tdTomato and FITC fluorescence intensities. The sorted cells were then centrifuged and fixed with PFA (4%). Finally, the cells were washed, fixed with PBS/mounting medium, and sandwiched between a coverslip and a glass slide sealed with nail polish.

SiRNA Knockdown

UACC-257 human melanotic melanoma cells were plated on six-well plastic-bottomed plate (Corning, Inc., Falcon™ 08-772-1H, Corning, N.Y.) at a density of 5×10$^5$ cells/well in 900 µL RPMI medium, to which a solution of 97 µL sodium acetate (25 mM), 2 µL lipidoid (1 mg/ml), and 1 µL pooled siRNA, GE Dharmacon, (10 µM) were added. Cells were kept in an incubator at 37° C. with 5% CO$_2$, and the media was changed every 24 hours for 4 days. On day 4, the cells were passaged and re-plated on a six-well glass-bottomed plate (In Vitro Scientific P06-14-0-N, Mountain View, Calif.) and placed in the incubator overnight to allow for imaging on day 5. The delay between initial treatment with siRNA and imaging is to allow for maximum phenotypic changes to occur within the cells.

Mouse Ear Imaging

For ex vivo mouse ear imaging, the ear tissue was acquired via ear punch (Φ=3 mm). A commercial hair removal lotion was used to wipe away most fine hairs from the ear tissue. The sample was then sandwiched between a coverslip and a glass slide, and imaged as described above. For in vivo mouse ear imaging, the mice were anesthetized with isoflurane mixed with 0.2 L/min oxygen and 0.8 L/min air via face mask. The fine hairs were removed using a commercial hair removal lotion, as in the ex vivo sample. The ear was then fixed onto a coverslip using double-sided tape, and imaged as described above. All studies and procedures involving animal subjects were approved by the Institutional Animal Care and Use Committee of Massachusetts General Hospital and were conducted strictly in accordance with the approved animal handling protocols.

Results

CARS Microscopy can be Used to Identify and Visualize Pheomelanin

Figure 4:
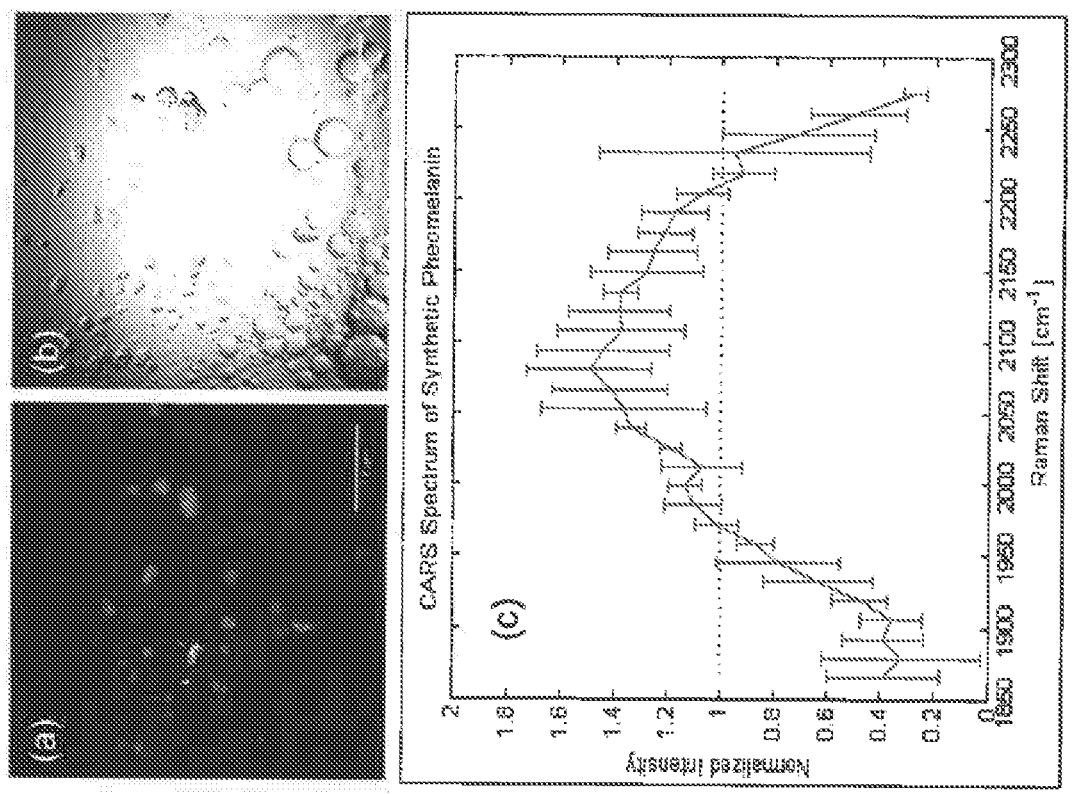
FIG. 4 shows results from imaging synthetic pheomelanin in a 4:1 water:hexane emulsion (scale bar: 50 μm), in which (a) shows a CARS image acquired at $\omega_P-\omega_S=2000$ cm$^{-1}$, where the pump and Stokes center wavelengths were respectively tuned to 861 nm and 1040 nm, (b) shows a trans-illumination image acquired with the 861 nm pump beam, and (c) shows the CARS spectrum of synthetic pheomelanin referenced to the wavelength-independent signal from a glass coverslip normalized by area under the curve.

It was demonstrated that CARS microscopy can be used to identify and visualize pheomelanin based on a unique, weak band of vibrational resonance centered at 2000 cm$^{-1}$. As shown in FIG. 4, synthetic pheomelanin, when distributed as small particles to eliminate heating, yielded a strong anti-Stokes CARS signal whose vibrational spectrum matches the weak band of vibration resonance of pheomelanin.

Imaging Isolated Melanocytes.

Figure 5:
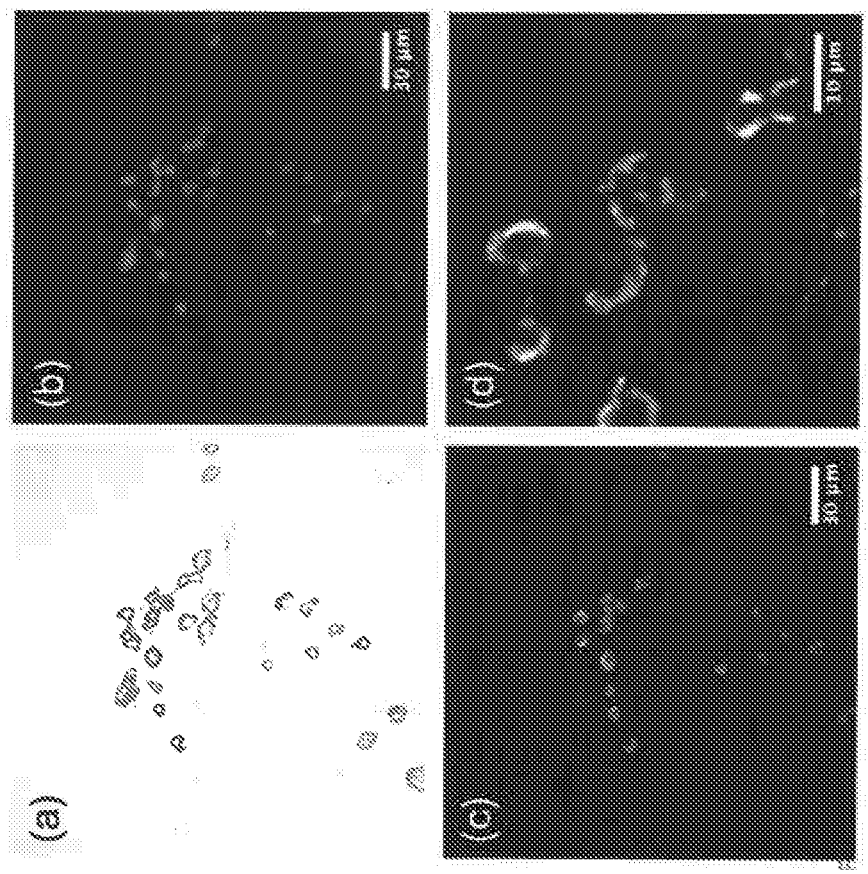
FIG. 5 shows results from imaging melanocytes isolated from red-haired C57BL/6 md1r$^{e/e}$ mice exhibit strong CARS signal at $\omega_P-\omega_S=2000$ cm$^{-1}$, where the pump and Stokes center wavelengths were respectively tuned to 877 nm and 1064 nm, in which (a) shows a trans-illumination image acquired with the 877 nm pump beam, (b) shows a confocal fluorescence image of tdTomato, (c) shows a false color CARS image mapping intracellular pheomelanin distribution, (d) shows a 4×-zoomed view of (c) showing the perinuclear distribution of signal intensity, consistent with the known biology of protective melanin caps in melanocytes.
Figure 6:
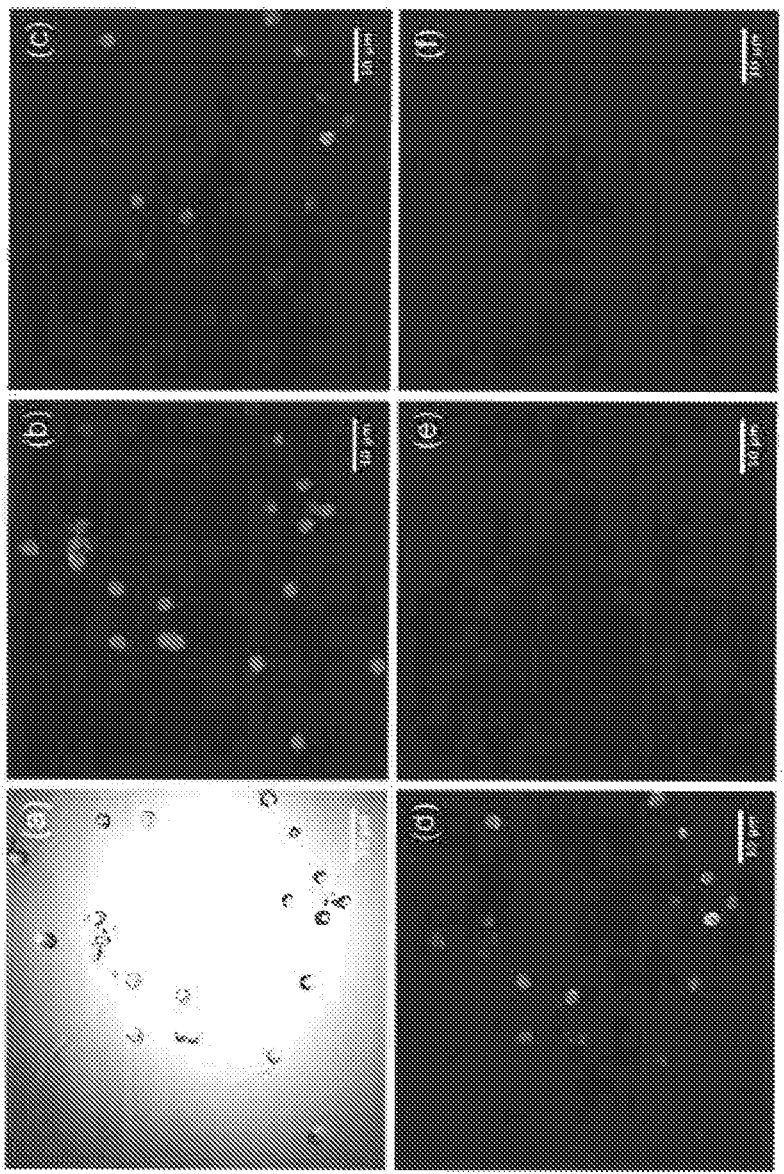
FIG. 6 shows results from imaging melanocytes isolated from albino-red C57BL/6 mc1r$^{e/e}$ Tyr$^{c/c}$ mice. Due to the albino allele (Tyr$^{c/c}$) these mice make no melanin species (including pheomelanin) and therefore serve as a negative control for imaging pheomelanin.

With knowledge of the pheomelanin vibrational spectrum, a protocol was developed to specifically visualize melanocytes known to only contain the red pigment. Isolated melanocytes were obtained from genetically controlled, Mc1r mutant red-head mice to observe the naturally synthesized pigment within cells. The Mc1r mutant red-head mice were additionally engineered to express either tdTomato or GFP on a melanocyte-specific promoter so as to enable FACS isolation of melanocytes. TdTomato Mice were sacrificed, their skin harvested, and dermal cells sorted based on the fluorescence of both tdTomato and FITC-labeled antibodies tagging c-Kit, a melanocyte surface marker. GFP-labeled mice were treated following a similar procedure, with melanocytes selected via their GFP signal. The sorted melanocytes were then fixed, sandwiched between a coverslip and a glass slide, and imaged with both CARS and confocal fluorescence microscopy. As shown in FIG. 5, the observed pheomelanin signals were not evenly distributed within melanocytes, but rather exhibited an asymmetric peri-nuclear appearance, consistent with the melanin cap formed by stage III/IV melanosomes to shield melanocytic DNA from UV radiation. As a control, genetically identical, tyrosinase-inactivated tdTomato albino-red-head mice were sacrificed and skin cells sorted to isolate individual melanocytes. No visible pheomelanin signals were observed with CARS microscopy (FIG. 6), further supporting the argument that the observed vibration signature indeed corresponds to pheomelanin.

Imaging Human Melanin

While the imaging performed on isolated melanocytes demonstrates the ability to visualize pheomelanin, the isolated melanocytes did not allow for an evaluation of dynamic transients in melanin production in living cells. Thus, in order to test whether changes in melanin production, especially pheomelanin production, can be detected, a human melanotic melanoma cell line (UACC-257) that produces a mixture of melanins dominated by eumelanin was selected for siRNA knockdown. In order to either promote pheomelanin production or halt melanin synthesis altogether, microphthalmia-associated transcription factor (MITF) and tyrosinase (Tyr) were targeted for siRNA knockdown, respectively.

Figure 7:
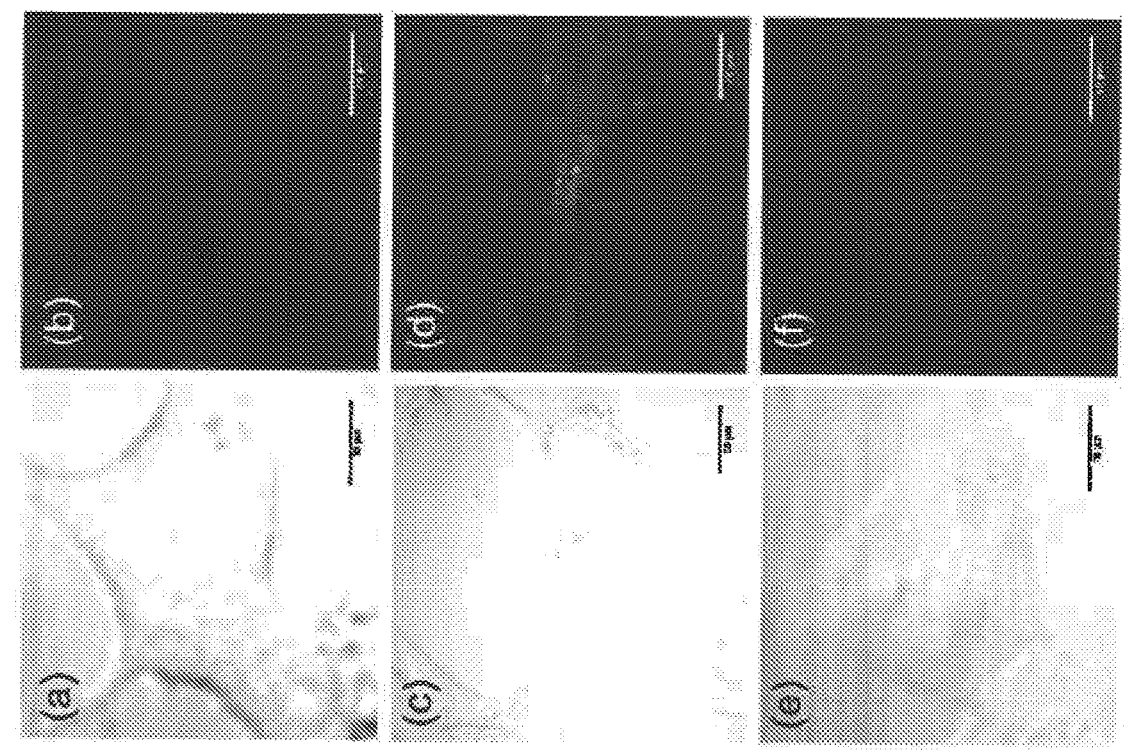
FIG. 7 shows results from imaging UACC-257 human melanoma cells following siRNA knockdown, which increases proportional pheomelanin levels, and is visualized using a CARS system tuned for imaging at 2000 cm$^{-1}$ ($\lambda_P$=861 nm; $\lambda_S$=1040 nm) to probe pheomelanin-specific molecular vibrations, in which (a) and (b) show a trans-illumination and a CARS image of cells treated with a control siRNA fragment that does not affect melanin production, (c) and (d) show a trans-illumination and a CARS image of cells treated with MITF siRNA to increase pheomelanin production, (e) and (f) show a trans-illumination and a CARS image of cells treated with tyrosinase siRNA to prevent production of both eumelanin and pheomelanin.

MITF is a transcription factor and downstream target of MC1R; it has been established that silencing of MITF can simulate the fair-skinned red-haired phenotype by favoring pheomelanin synthesis. Tyrosinase, on the other hand, is an oxidase that is crucial in the early stages of melanin production. Therefore, silencing of tyrosinase halts production of both pheomelanin and eumelanin altogether. To control for any non-specific effects of siRNA fragments, an additional population of cells was treated with a negative control fragment of siRNA that does not affect a target involved in melanin production. As in the experiments described above, the CARS system was tuned for imaging at the 2000 cm$^{-1}$ band to probe the pheomelanin-specific molecular vibration. FIG. 7 shows both the trans-illumination and CARS image sets of cells treated with control, MITF, and tyrosinase siRNA fragments. Compared to the control group, the MITF-knockdown cells showed a significant increase in pheomelanin signal in the form of punctate bodies scattered across the intracellular periphery. These signals correspond to melanosomes, which are known to extend into the melanocyte dendrites in order to deliver melanin to keratinocytes. It should be noted that no melanin cap is formed in melanocyte cultures in vitro, which is attributed to the absence of extracellular spatial cues. In contrast, the tyrosinase knockdown cells show a nearly complete elimination of all CARS signal, indicating an extremely low level of pheomelanin production.

Imaging Intact Skin

Figure 8:
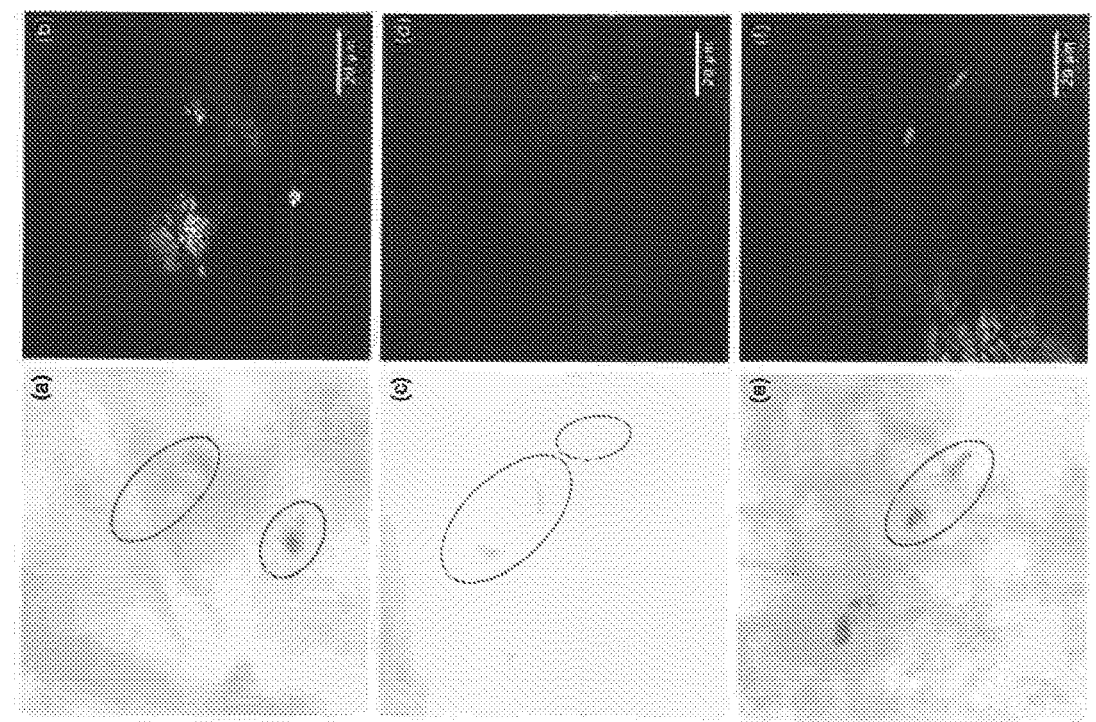
FIG. 8 shows results from imaging pheomelanin stores in a red-haired mouse ear, in which (a), (c), and (e) show bright-field trans-illumination images acquired from a microscope eyepiece, (b), (d), and (f) show a maximal projection view of CARS image stack of the mouse ear where a non-resonant CARS stack (acquired with the pump beam set to 871 nm, $\omega_P$-$\omega_S$=1866 cm$^{-1}$) was subtracted from the image stack acquired with the pump beam set to 861 nm ($\omega_P$-$\omega_S$=2000 cm$^{-1}$) to minimize the non-resonant signal contribution from structures other than pheomelanin. Image stacks are 27 µm thick, with a step size of 1 µm), showing bright granules from the pheomelanin stores within melanocytes and at the base of the hair follicle.
Figure 9:
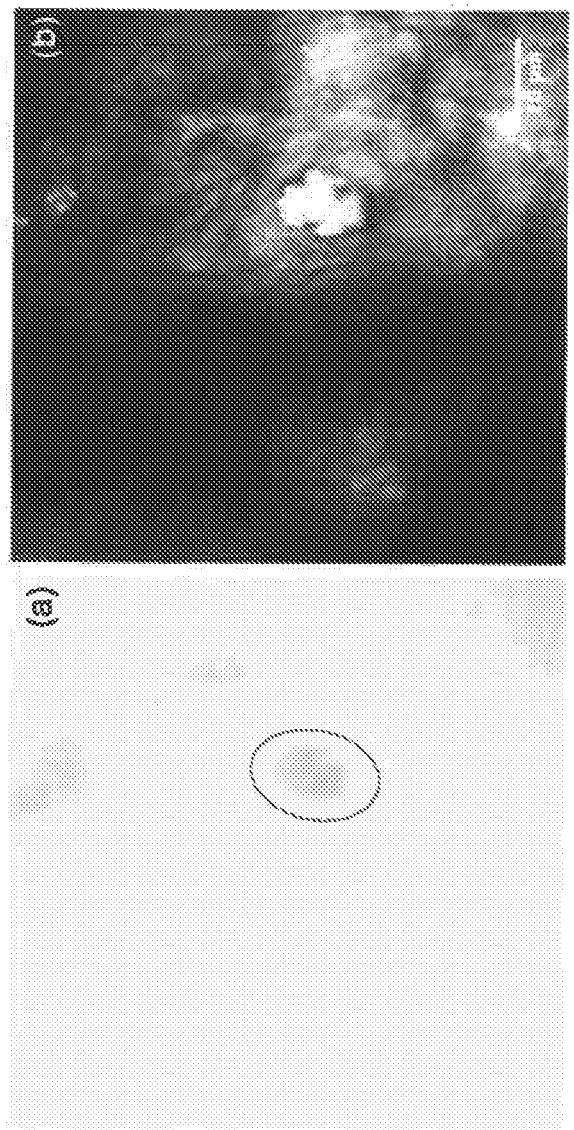
FIG. 9 shows results from imaging pheomelanin stores in a red haired mouse ear in vivo, in which (a) shows a bright-field trans-illumination image acquired from a microscope eyepiece and (b) shows a maximal projection view of a CARS image stack (acquired with the pump beam set to 871 nm ($\omega_P$-$\omega_S$=1866 cm$^{-1}$) was subtracted from the image stack acquired with pump beam set to 861 nm ($\omega_P$-$\omega_S$=2000 cm$^{-1}$) to minimize the non-resonant signal contribution from structures other than pheomelanin) of the mouse ear, showing bright granules from the pheomelanin stores.

Intact ex vivo ear skin from a red-haired mouse was imaged using CARS. The resulting CARS images from a mouse ear showed bright granules from the pheomelanin stores within melanocytes and at the base of the hair follicle. The pump beam was set to 871 nm ($\omega_P-\omega_S=1866$ cm$^{-1}$) to generate non-resonant background signal for post-processing correction, and set to 861 nm ($\omega_P-\omega_S=2000$ cm$^{-1}$) to generate resonant CARS signals from pheomelanin. The ear of a mouse is thin, so bright field images can simultaneously be acquired alongside CARS as a reference. As shown in the bright-field image (FIGS. 8(a), (c) and (e)), pheomelanin stores appear reddish-brown, with visible cell bodies and dendrites. FIGS. 8(b), (d) and (f) show CARS z-stack projections acquired at the same field of view as the trans-illumination images, corrected to minimize the non-resonant background. Pheomelanin stores with punctate structures showing bright CARS signals were observed at areas surrounding sebaceous glands at the base of an individual hair (white structure in the top left quarter of FIG. 8(b)). This matches the known localization pattern of eumelanin-containing melanocytes in the C57BL/6 parent mouse strain (data not shown). Individual pheomelanotic granules can be distinctly visualized and co-localized with the pigmented areas observable by bright-field microscopy, highlighting the submicron resolution of the developed CARS imaging system. Similar image features were found repeatedly in FIGS. 8(d) and (f). To ensure that the pheomelanotic stores are not an artifact of the ex vivo condition, in vivo imaging was carried out on the ears MC1R Cre-Lox mice. Indeed, pheomelanin stores were found in living mice (FIG. 9). Notably, both ex vivo and in vivo ears of the control albino-red and albino mice were imaged, with no visible pheomelanin signals observed.

To confirm these measurements with the gold standard of histology, thin sections (5 μm in thickness) were prepared from the red-haired mouse ear. As traditional H&E stain is not able to distinguish pheomelanin from other structures inside the skin, only a light-colored hematoxylin stain was used. Pheomelanin aggregates can be identified as light brown-pigmented regions primarily located at the epidermis and dermis above the cartilage layer. These regions were confirmed to contain pheomelanin via standard Raman spectroscopy (data not shown).

Amelanotic Melanoma

Figure 10:
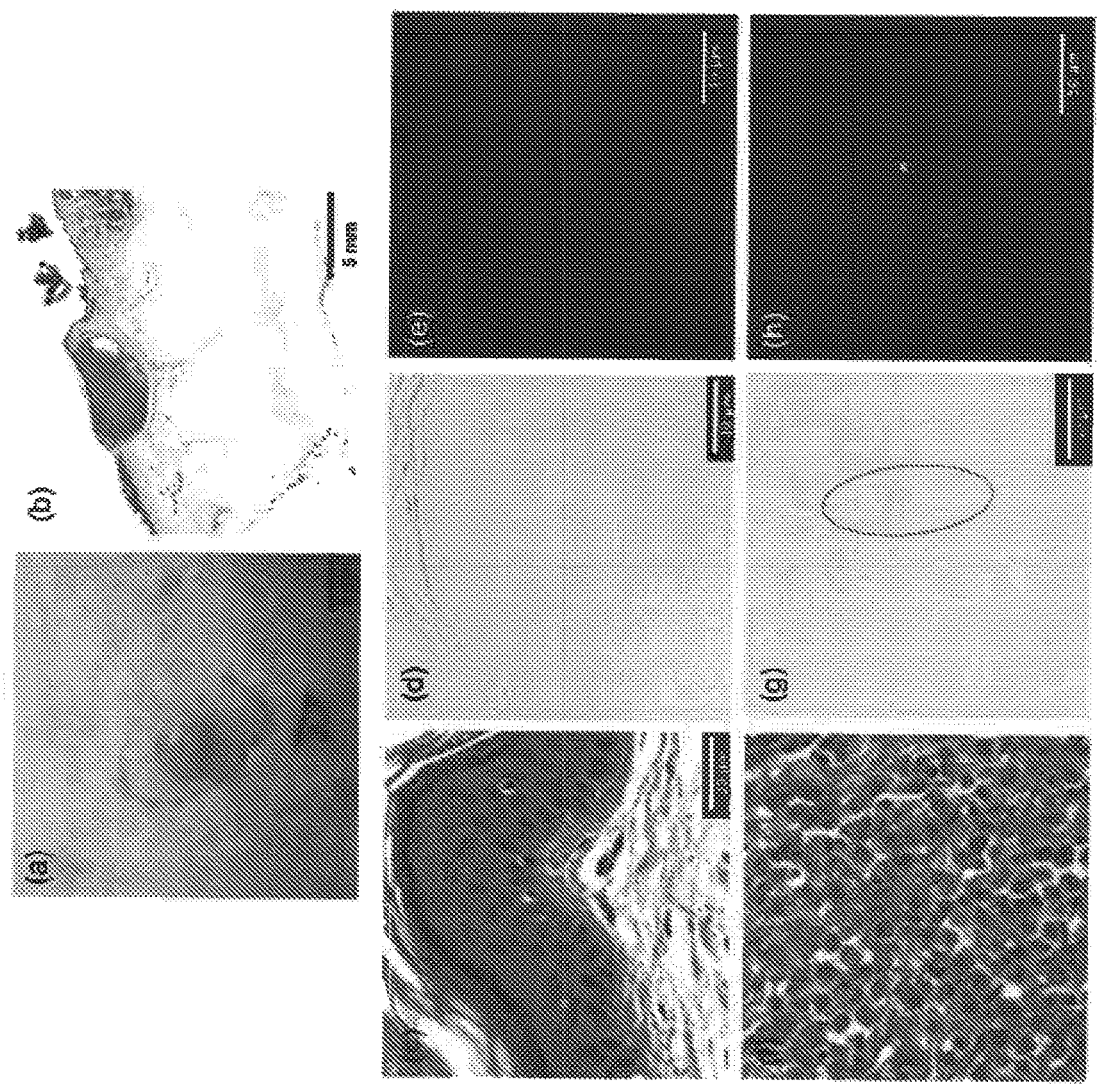
FIG. 10 shows results from imaging human amelanotic melanoma (deemed amelanotic on the basis of lack of dark pigmentation when examined by eye in the patient's skin), in which (a) shows a clinical picture of an amelanotic melanoma lesion, (b) shows an H&E stain of the patient slide (×10 magnification), (c) shows a zoomed in view of the perilesional skin showing normal architecture of both epidermis and dermis, (d) shows a bright-field trans-illumination image acquired from the microscope eyepiece from the perilesional area, (e) shows an epi-CARS image of the same perilesional area compared to (d) (image acquired with pump beam wavelength at 841 nm (ωp–ωs=2275 cm$^{-1}$) was subtracted from the image acquire with pump beam wavelength at 855 nm (ωp–ωs=2081 cm$^{-1}$) to minimize the non-resonant background from structures other than pheomelanin; (f) shows a zoomed-in view of the amelanotic melanoma area showing high density of cells with no obvious sign for melanin; (g) shows a bright-field trans-illumination image acquired from the microscope eyepiece from an unstained slide of the melanoma area showing slightly pigmented granular structures (circle), (h) shows an epi-CARS image of the same tumor area compared to (g), with the same settings as for (e). Saturated bright pheomelanin signals were found (circle) corresponding very well with the slightly pigmented area shown in (g)
Figure 11:
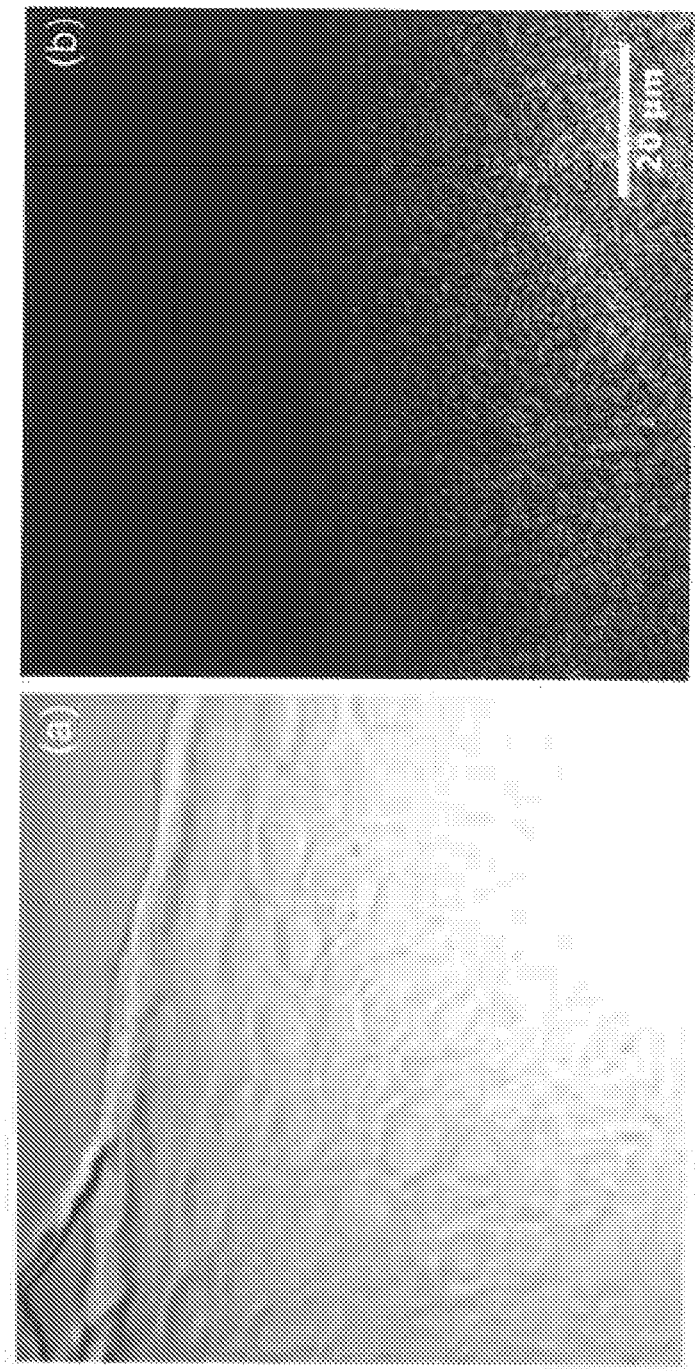
FIG. 11 shows results from imaging the perilesional normal area of an amelanotic melanoma patient slide, in which (a) shows a bright-field trans-illumination image acquired from a microscope eyepiece and (b) shows a CARS image of an amelanotic melanoma patient slide (acquired with the pump beam set to 841 nm ($\omega_P$-$\omega_S$=2275 cm$^{-1}$) was subtracted from the image acquired with the pump beam set to 855 nm ($\omega_P$-$\omega_S$=2081 cm$^{-1}$) to minimize the non-resonant signal contribution from structures other than pheomelanin). No bright granules from pheomelanin aggregates were observed in the CARS image of the healthy skin surrounding the melanoma lesion.

CARS imaging and spectroscopic measurements were performed on fixed and unstained sections (10 μm in thickness) from an amelanotic melanoma patient. Clusters of reddish-brown submicron granules can be seen in the bright-field image within the melanoma lesion area (FIG. 10(g)). Strong, almost saturating, CARS signals were observed, indicating an extremely high density of pheomelanin within the granules, as shown in FIG. 10(h). The peri-lesional healthy skin was also imaged, where only low levels of pheomelanin CARS signals were observed; no high-density pheomelanin aggregates could found (FIG. 11). This evidence suggests not only that amelanotic melanoma lesions can actually contain dense stores of pheomelanin, but that these deposits may be detected noninvasively using CARS imaging.

From the above description, those skilled in the art will perceive improvements, changes and modifications. Such improvements, changes and modifications are within the skill of one in the art and are intended to be covered by the appended claims.

What is claimed is:

1. A system comprising:
   an imaging system to record a signal based on a presence of melanin in tissue comprising:
      a first laser source to emit a Stokes pulse train comprising a first center wavelength or frequency;
      a second laser source to emit a pump pulse train comprising a second center wavelength or frequency,
      wherein an energy difference between the Stokes pulse train and the pump pulse train is from 1750 $cm^{-1}$ to 2250 $cm^{-1}$,
      wherein the Stokes pulse train and the pump pulse train overlap in space and time to image the tissue;
      a scanning mechanism to focus a combination of the Strokes pulse train and pump pulse train within the tissue and scan across the tissue;
      a detector to detect the signal based on a presence of melanin within the tissue, wherein the signal comprises a coherent anti-Stokes Raman scattering (CARS) signal and a modulation transfer signal; and
      a display device to display an image based on the signal to visualize the melanin present in the tissue.

2. The system of claim 1, wherein a ratio of power for the pump pulse train to the Stokes pulse train is about 1.5 to 1 so as to not cause changes in the melanin in the tissue.

3. The system of claim 1, wherein the detector detects the signal in the epi direction.

4. The system of claim 1, wherein the CARS signal and/or at least a portion of the modulation transfer signal arises due to an interaction of the Stokes pulse train and the pump pulse train with at least a portion of the melanin in the tissue.

5. The system of claim 1, wherein the CARS signal and the modulation transfer signal enable at least one of eumelanin and pheomelanin to be distinguishable in the image.

6. The system of claim 1, wherein a duration of Stokes pulses within the Stokes pulse train and pump pulse train within the pump pulse train is from 90 fs to 7 ps; and
   wherein a repetition rate of the pump pulse train and Stokes pulse train is set to a common value between 76 MHz and 82 MHz.

7. The system of claim 1, wherein the Stokes pulses and the pump pulses are unchirped and compensated by positive or negative group velocity dispersion optics.

8. The system of claim 1, wherein the first center wavelength between 1040 nm and 1064 nm and the second center wavelength between 841 nm and 888 nm.

9. A method comprising:
   configuring a first laser source to deliver a Stokes pulse train, wherein the Stokes pulse train comprises a first center wavelength;
   configuring a second laser source to deliver a pump pulse train, wherein the pump pulse train comprises a second center wavelength,
   wherein an energy difference between the Stokes pulse train and the pump pulse train is between 1750 $cm^{-1}$ to 2250 $cm^{-1}$;
   irradiating tissue with the Stokes pulse train and the pump pulse train focused within the tissue, wherein the Stokes pulse train and the pump pulse train overlap in space and time;
   detecting a signal based on a presence of melanin within the tissue wherein the signal comprises a coherent anti-Stokes Raman scattering (CARS) signal and a modulation transfer signal; and
   displaying an image based on the signal to visualize the melanin within the tissue.

10. The method of claim 9, wherein the energy difference between the Stokes pulse train and the pump pulse train is further between 1850 $cm^{-1}$ to 2150 $cm^{-1}$.

11. The method of claim 9, wherein the energy difference between the Stokes pulse train and the pump pulse train is further between 1950 $cm^{-1}$ to 2050 $cm^{-1}$.

12. The method of claim 9, wherein the irradiating further comprises irradiating the tissue within a body of a live patient.

13. The method of claim 9, wherein the CARS signal and the modulation transfer signal arise due to a interaction of the Stokes pulse train and the pump pulse train with the melanin within the tissue.

14. The method of claim 9, wherein the CARS signal and the modulation transfer signal allow for a visualization distinguishing between eumelanin and pheomelanin within the tissue in the image.

15. The method of claim 9, wherein the first center wavelength is within a range from 1040 nm to 1064 nm and the second center wavelength is within a range from 841 to 888 nm.

16. The method of claim 15, wherein a duration of pump pulses within the pump pulse train and Stokes pulses within the Stokes pulse train is from 90 fs to 7 ps, and
   wherein a repetition rate of the pump pulse train and Stokes pulse train is set to a common value between 76 MHz and 82 MHz.

17. A portable imaging probe comprising:
   a scanning mechanism to focus a Stokes pulse train and a pump pulse train within tissue while scanning across the tissue, wherein the Stokes pulse train comprises a first center wavelength and the pump pulse train is tuned to a second center wavelength,
   wherein an energy difference between the Stokes pulse train and the pump pulse train is between 1750 $cm^{-1}$ and 2250 $cm^{-1}$,
   wherein the Stokes pulse train and the pump pulse train overlap in space and time to image the tissue; and
   a detector to detect a signal based on a presence of melanin within the tissue, wherein the signal comprises a coherent anti-Stokes Raman scattering (CARS) signal and a modulation transfer signal.

18. The portable imaging probe of claim 17, wherein the coherent anti-Stokes Raman scattering (CARS) signal and the modulation transfer signal arise due to interaction of the Stokes pulse train and the pump pulse train with the melanin in the tissue, and
   wherein the CARS signal and the modulation transfer signal distinguish between eumelanin and pheomelanin within the tissue.

19. The portable imaging probe of claim 17, wherein the tissue comprises skin and at least a portion of the portable device is handheld.

20. The portable imaging probe of claim 17, wherein the first center wavelength is between 1040 nm and 1064 nm and the second center wavelength is between 841 and 888 nm.

* * * * *